United States Patent [19]

George

[11] 4,167,880

[45] Sep. 18, 1979

[54] WATER COUPLED ULTRASONIC THROUGH TRANSMISSION APPARATUS

[75] Inventor: Loyd W. George, Renton, Wash.

[73] Assignee: The Boeing Company, Seattle, Wash.

[21] Appl. No.: 908,299

[22] Filed: May 22, 1978

[51] Int. Cl.[2] .......................................... G01N 29/00
[52] U.S. Cl. ........................................................ 73/644
[58] Field of Search .................. 73/644, 596, 661, 665

[56] References Cited

U.S. PATENT DOCUMENTS

| | | | |
|---|---|---|---|
| 3,625,051 | 9/1969 | Uozumi | 73/644 X |
| 3,662,590 | 5/1972 | Shiraiwa et al. | 73/644 |
| 3,745,833 | 7/1973 | Armstrong | 73/644 X |

Primary Examiner—Jerry W. Myracle
Attorney, Agent, or Firm—Conrad O. Gardner; B. A. Donahue

[57] ABSTRACT

An ultrasonic non-destructive testing apparatus utilizing through transmission water jet coupling. Through transmission is provided along an arcuate path which includes paired exit path portions of the apparatus. Sound is transmitted through the bent liquid column via transmitting and receiving transducers upstream of the respective paired exit path portions.

2 Claims, 4 Drawing Figures

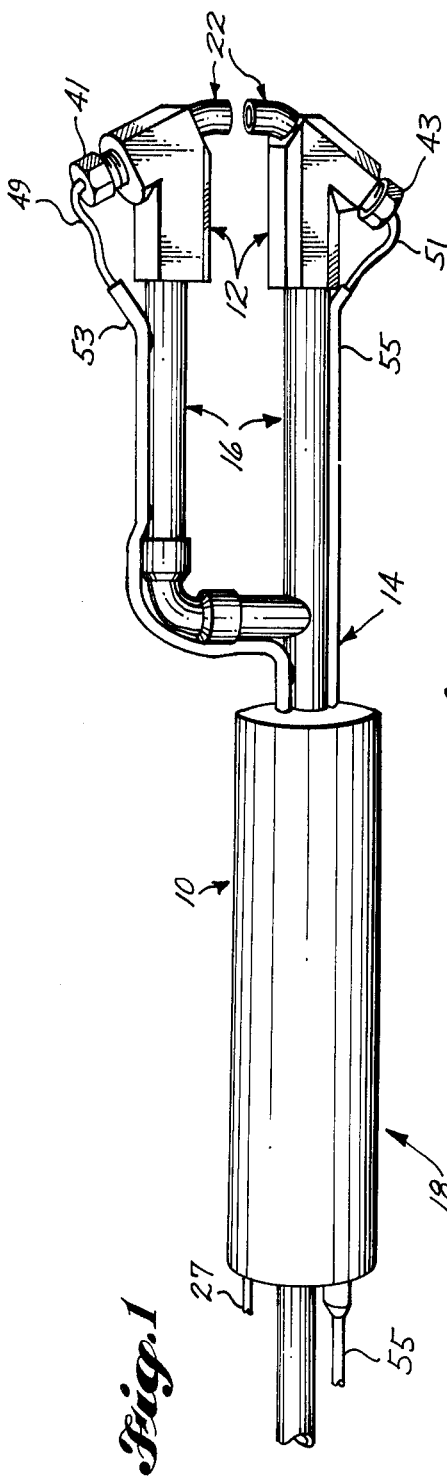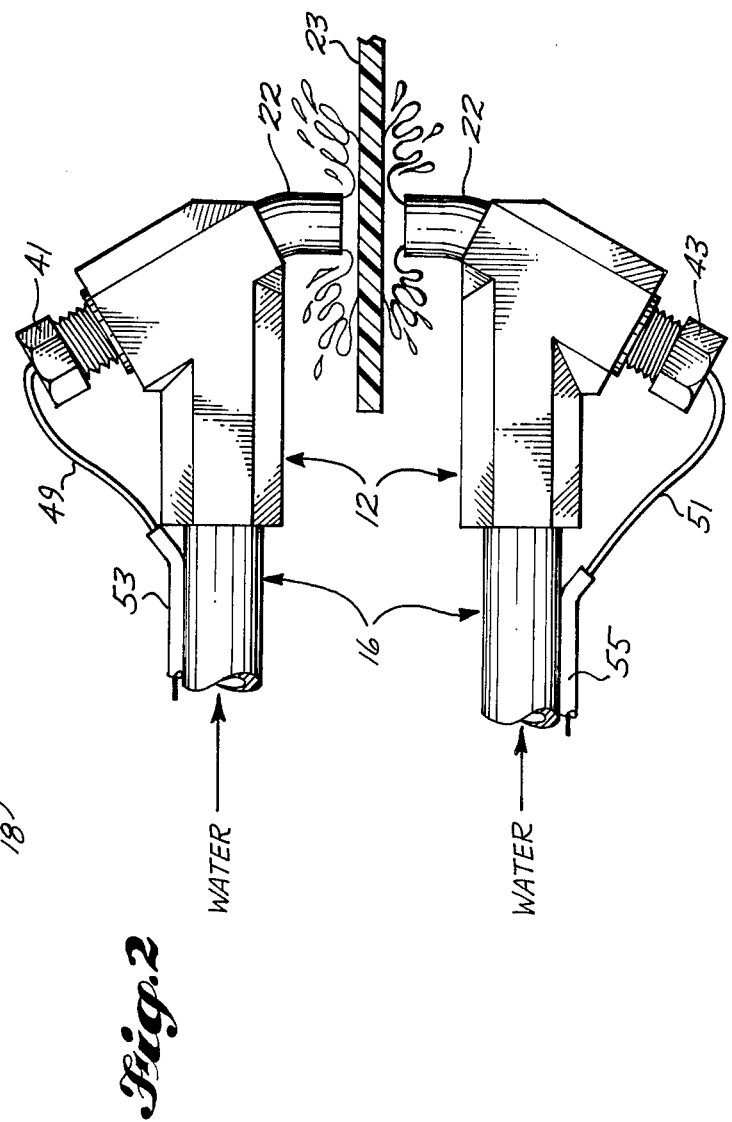

WATER COUPLED ULTRASONIC THROUGH TRANSMISSION APPARATUS

This invention relates to water jets for ultrasonic inspection and more particularly to such apparatus having paired exit path portions.

A prior art air backed transducer element having a liquid flow over a frontal major surface area of the transducer is shown in my U.S. Pat. No. 4,004,736 in an ultrasonic water jet which direct transducer element mounting configuration as in the hereinafter described mounting arrangement provides simplicity and cost effectiveness in transducer mounting arrangements.

Dual ultrasonic water jets are shown in British Pat. Nos. 1,089,742 and 1,436,147, British Pat. No. 1,089,742 relating to a method and apparatus for the non-destructive testing and detection of internal faults in revolving bodies utilizing ultrasonic impulses, while British Pat. No. 1,436,147 relates to a device for the continuous ultrasonic examination of a rolled strip.

It is an object of the present invention to provide dual ultrasonic water jets having air backed transducer elements.

It is a further object to provide water coupled through transmission ultrasonic inspection apparatus in which the acoustically modulated stream includes a plurality of arcuate path portions intermediate the transmitting and receiving transducer elements.

It is yet another object of this invention to provide dual ultrasonic water jet apparatus including bent exit path tip portions for inspection of structures disposed between the exit path tip portions thereby enabling inspection of such structures in heretofore difficult to reach locations.

The foregoing and other objects and advantages of this invention will best be understood by the following detailed description of an embodiment thereof taken in view of the accompanying drawings, wherein:

FIG. 1 is a perspective view of a preferred embodiment of the present dual ultrasonic jet apparatus;

FIG. 2 is a perspective view of the dual ultrasonic jet apparatus of FIG. 1 showing the apparatus deployed in operation about a composite structure being tested;

Figure 4:
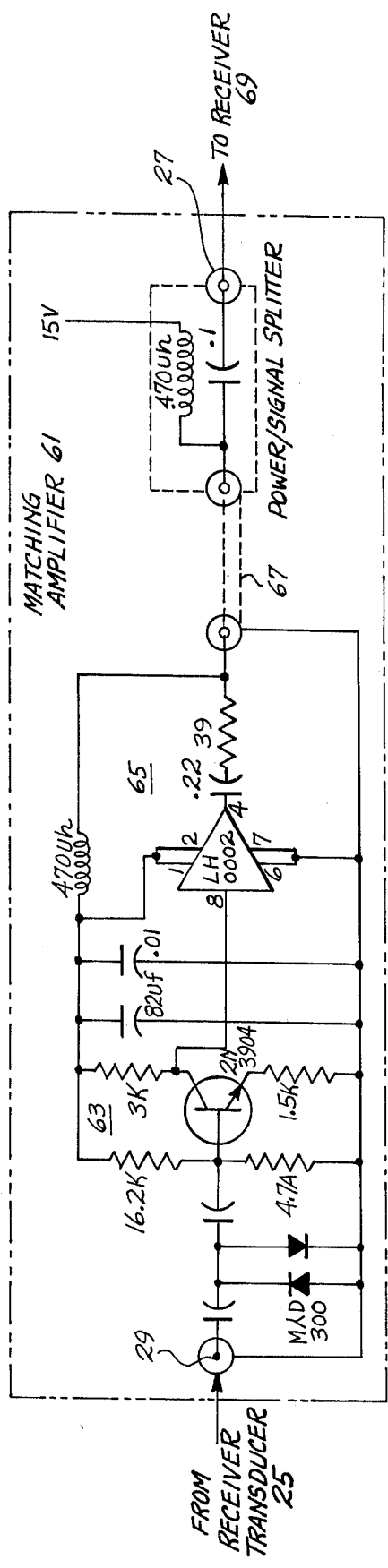
Figure 3:
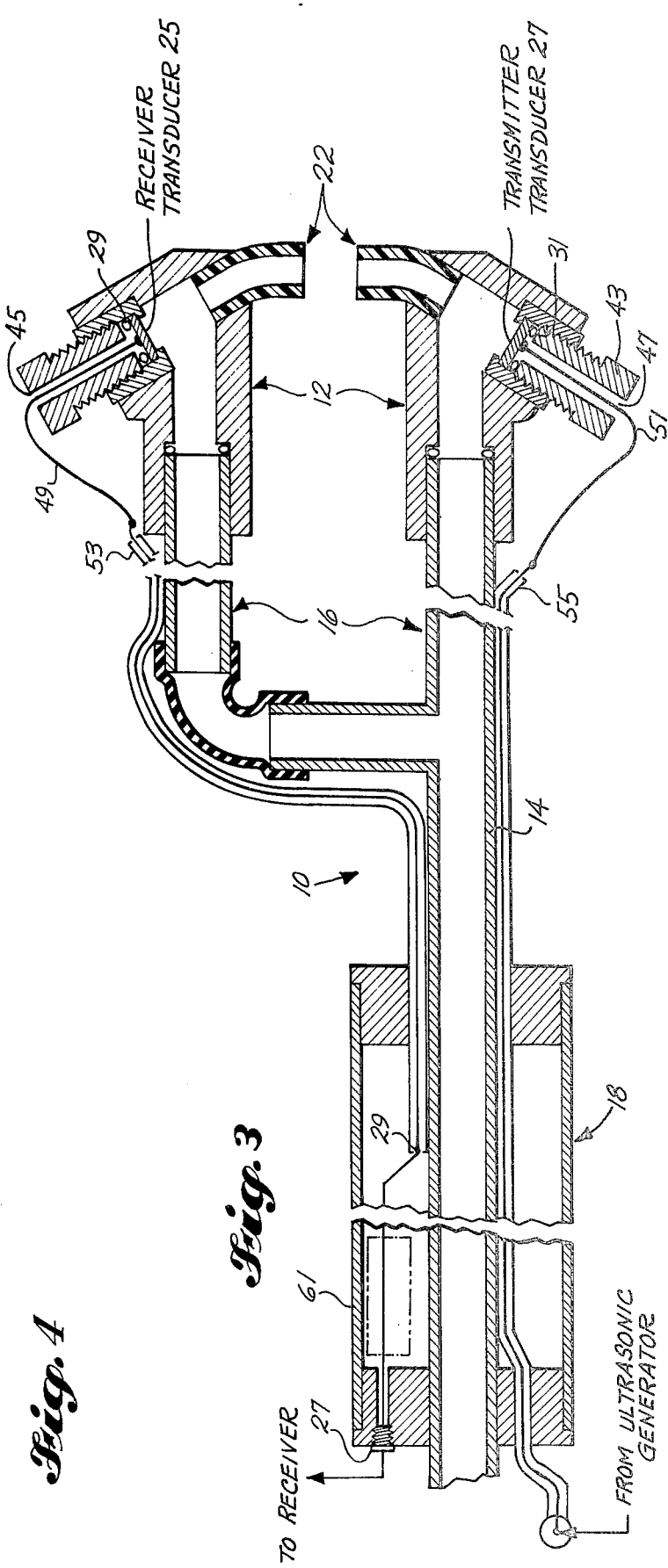
FIG. 3 is a detailed cross sectional view of the dual ultrasonic jet apparatus shown in FIGS. 1 and 2; and, FIG. 4 is a circuit schematic diagram of the matching amplifier and power/signal splitter shown in the handle portion of the dual ultrasonic water jet apparatus of FIG. 3.

Referring now in detail to the drawings, especially of FIG. 1 thereof, it will be observed that dual ultrasonic water jet apparatus 10 comprises a pair of transducer and nozzle housing sections 12, a water conduit 14 terminating at one end in branched U-shaped end portion 16 to which is attached housing sections 12 and cylindrically shaped handle assembly 18 which is coaxially disposed about cylindrically shaped water conduit 14. Cylindrically shaped handle assembly 18 provides housing means as seen in FIG. 3 for the matching amplifier and power/signal splitter hereinafter shown and described in FIG. 4. Cylindrically shaped water conduit 14 including terminating U-shaped end portion 16 comprised brass tubing in the preferred embodiment herein shown and described. Curved nozzle tips 22 permit close access of water path coupling from both sides of flanges or ribs 23 as shown in FIG. 2, thereby providing a through transmission path for an acoustically modulated stream from transmitter transducer 27 to receiver transducer 25 (as seen in FIG. 3). Disk type receiving and transmitting transducers 25 and 27 are mounted respectively (as seen in FIG. 3) on compressible rubber O-rings 29 and 31 which provide an electrically insulative and water tight support for the major surface of the transducers opposite the water flow path provided during operation through the branches of U-shaped conduit end portion 16. Such air backed transducer element mounting is similar to that shown in aforementioned U.S. Pat. No. 4,004,736 and having certain of the attendant advantages thereof also hereinbefore discussed.

Referring now more specifically to the detailed cross sectional view of FIG. 3 of the present dual ultrasonic jet apparatus providing through transmission coupling it should be noted that a pair of transducer holders 41 and 43 are inserted into the respective nozzle housings 12 behind the respective electrically insulative and watertight compressible rubber O-rings 29,31. Transducer holders 41 and 43 are provided with coaxially disposed central passages 45 and 47 permitting receiving and transmitting transducer leads 49 and 51 to be connected from respective receiving and transmitting transducers 25 and 27 to solid sheath coaxial transmission lines 53 and 55 respectively. In operation of the ultrasonic jet apparatus of FIG. 3, transmission line 55 is coupled to an ultrasonic generator (not shown) to provide the flow of suitable ultrasonic energy to transmitter transducer element 27 for ultrasonic inspection. Transmission line 53 is coupled (as seen in FIG. 3) to matching amplifier 61 disposed within cylindrically shaped handle assembly 18, the output of matching amplifier 61 at coaxial connector 27 being connected in operation to suitable receiving means (not shown). Matching amplifier 61 is shown in more detail in the FIG. 4 electrical schematic thereof and may be seen to comprise a first stage 63 medium impedance input amplifier for providing impedance matching from receiver transducer 25 and a second stage 65 line driver providing impedance matching to putput transmission line 67. Power/signal splitter 69 as such nomenclature implies, provides D.C. power from signal isolation thereby permitting the 15 volts D.C. shown which powers matching amplifier 61 to be carried on the same lead as the signal information and separated therefrom prior to coupling of the information signal at 27 on to the receiver.

Nozzle housing sections 12 besides providing support for receiving and transmitting transducers 25 and 27 via transducer holders 41 and 43 hereinbefore discussed further include exit path portions comprising curved nozzle tips 22 which comprised nylon tubing sections.

It was discovered that although an arcuate path (not a straight line path) was provided for the acoustically modulated stream (between the central axis of a major surface area of the disk shaped piezo electric transmitting transducer 27 and the central axis of a major surface area of the disk shaped piezo electric receiving transducer 25) with intermediate through transmission of acoustical energy provided by direct coupling through test number 23, such arcuate path still resulted in the transmission of sound through a bent water column between transducers. Other features and advantages including easy replacement or substitution of variously sized curved nozzle tip portions 22 thus facilitating various sized test member 23 testing, and simplified receiver and transmitter transducer 25 and 27 replacement can be seen to flow from the hereinbefore described dual ultrasonic water jet apparatus 10.

I claim:

1. In combination in an apparatus providing through transmission water jet coupling for the nondestructive testing of a test member having first and second major surface area portions: a first water flow path having an arcuate path portion arranged to direct a stream of water against said first major surface area portion of said test member; a transmitting transducer disposed upstream from said arcuate path portion of said first water flow path for providing modulation of said first water flow path with ultrasonic energy, a second water flow path having an arcuate path portion arranged to direct a stream of water against said second major surface area portion of said test member; a receiving transducer disposed upstream from said arcuate path portion of said second water flow path for receiving ultrasonic energy transmitted through said test member and coupled to said second water flow path.

2. A non-destructive testing apparatus for providing through transmission water jet coupling of ultrasonic energy comprising in combination:

a tubular cylindrically shaped water conduit terminating at one end in a U-shaped portion wherein each of the ends of said U-shaped portion includes a nozzle housing section connected thereto;

each of said nozzle housing sections having an air backed transducer element mounted therein;

each of said nozzle housing sections having means for providing an arcuate water flow path downstream of said air backed transducer element;

a cylindrically shaped handle assembly coaxially disposed about said tubular cylindrically shaped water conduit; and matching amplifier circuit means disposed within said cylindrically shaped handle assembly.

* * * * *